United States Patent [19]

Sander et al.

[11] Patent Number: 4,597,738
[45] Date of Patent: Jul. 1, 1986

[54] ORTHODONTIC DEVICE

[75] Inventors: Günter Sander, Ulm; Rolf Förster, Pforzheim, both of Fed. Rep. of Germany

[73] Assignee: Bernhard Forster GmbH, Pforzheim, Fed. Rep. of Germany

[21] Appl. No.: 708,709

[22] Filed: Mar. 6, 1985

[30] Foreign Application Priority Data

Mar. 30, 1984 [DE] Fed. Rep. of Germany ....... 3411852

[51] Int. Cl.4 .............................................. A61C 3/00
[52] U.S. Cl. .......................................... 433/7; 433/19
[58] Field of Search ...................................... 433/19, 7

[56] References Cited

U.S. PATENT DOCUMENTS

| 4,026,023 | 5/1977 | Fisher | 433/7 |
| 4,416,626 | 11/1983 | Bellavia | 433/7 |
| 4,462,799 | 7/1984 | Nardella | 433/19 |

FOREIGN PATENT DOCUMENTS

| 1041207 | 10/1958 | Fed. Rep. of Germany | 433/7 |
| 1110363 | 7/1961 | Fed. Rep. of Germany | 433/19 |
| 2703820 | 8/1978 | Fed. Rep. of Germany | 433/7 |

Primary Examiner—John J. Wilson
Attorney, Agent, or Firm—Balogh, Osann, Kramer, Dvorak, Genova & Traub

[57] ABSTRACT

An orthodontic device includes an upper jaw thrust plate and a lower jaw thrust plate. These plates are connected to the teeth and are provided in the front teeth region with activating rods and slideways respectively, cooperating to effect a sagittal displacement of the jaws relative to each other. Two treatment stages are to be combined and an optimum result of the treatment within a reduced time is to be ensured. The upper or lower jaw thrust plate includes two sections, which are connected by a jackscrew mechanism, to which the activating rods are secured.

9 Claims, 10 Drawing Figures

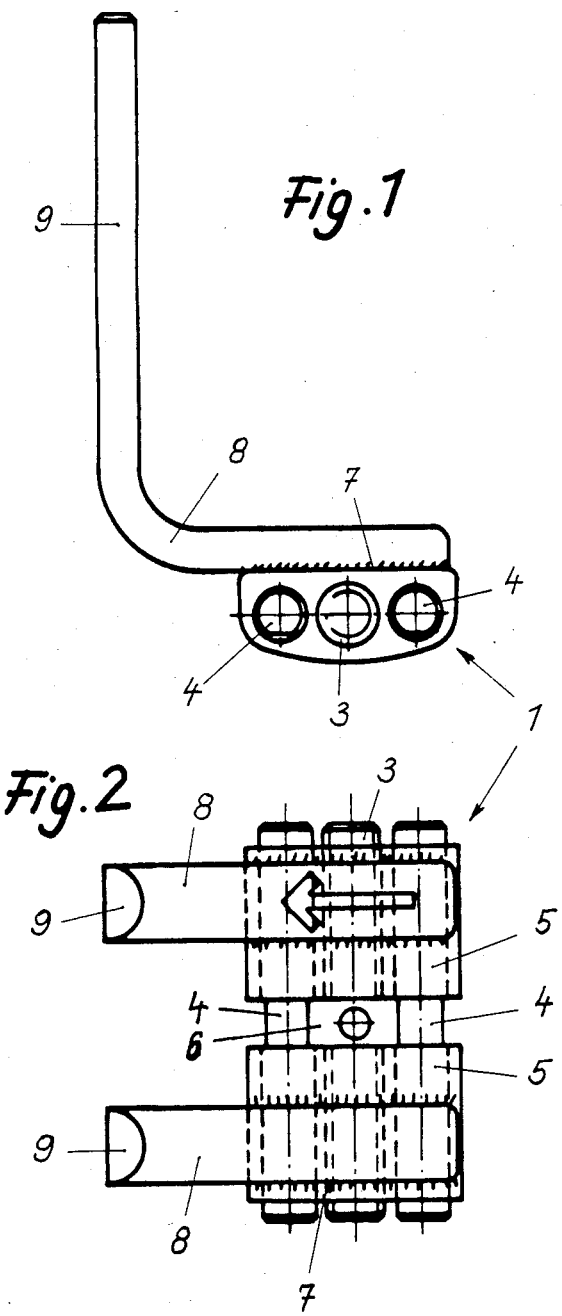

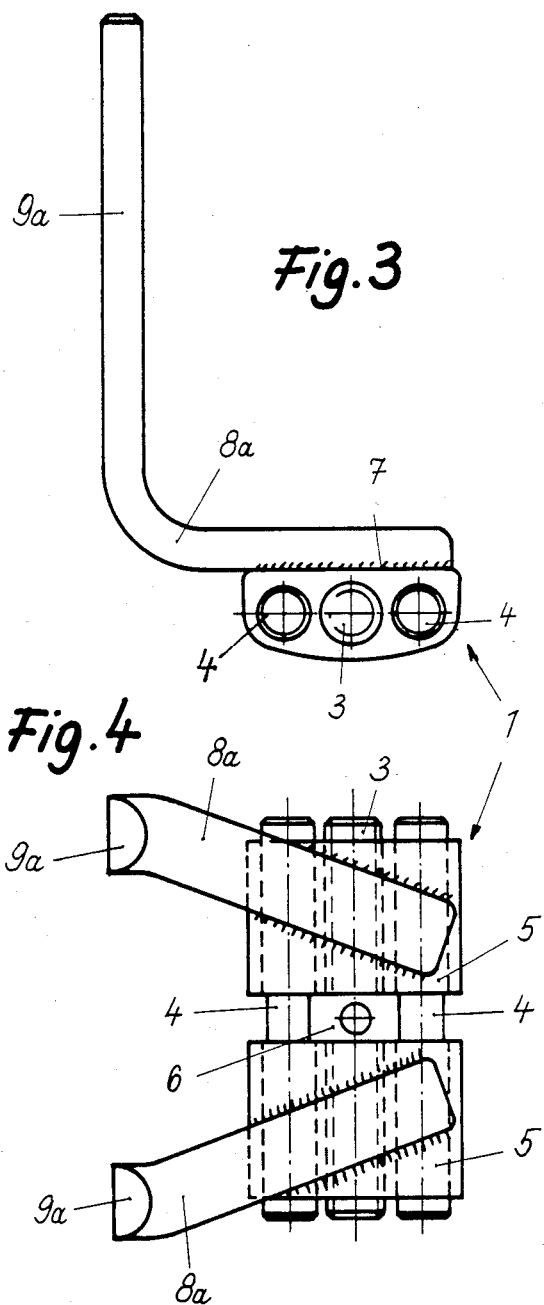

ORTHODONTIC DEVICE

BACKGROUND OF THE INVENTION

1. Field of the Invention

This invention relates to an orthodontic device comprising an upper jaw thrust plate and a lower jaw thrust plate, which are connected to the teeth and used for a sagittal treatment effected by a cooperation between activating rods and slideways in the front teeth region so as to displace the jaws relative to each other.

2. Description of the Prior Art

Such thrust plates serve to correct a condition which is described as supraocclusion and in which the lower jaw is excessively set back from the upper jaw. The thrust plates consist of an upper jaw thrust plate and a lower jaw thrust plate. Two activating rods are embedded in the upper jaw thrust plate and bear under initial stress on an inclined planar surface provided on the lower jaw thrust plate adjacent to the front teeth and during an opening and closing of the jaws exert a force which tends to correct the sagittal setback of the lower jaw. This action requires the dental arches of the upper and lower jaws to be adjusted relative to each other in the transversal direction so that the treatment for correcting supraocclusion must be preceded by a treatment taking about 1½ years. The subsequent treatment for adjusting the supraocclusion or subocclusion, the opposite condition, takes additional 1½ years so that the total treatment can only be effected as long as a growth, i.e., a rearrangement of muscles, is taking place so that there is a change of the articulated joints. Because the treatment cannot begin before the temporary teeth have been replaced and cannot be performed as long as there is growth, the success of the treatment depends highly on growth, which takes place only for a limited time, which cannot be exactly predicted.

An additional difficulty arising in the manufacture of the known devices resides in that the rods which slide on the inclined planar surface must be embedded in the thrust plate to extend absolutely parallel to the plane of the surface because an additional torque will otherwise be exerted on a jaw arch. On the other hand, the inclined planar surface of the lower jaw thrust plate must be parallel to the activating rods and must be arranged at such an angle that a forward thrust for a sagittal correction of the lower jaw is produced.

SUMMARY OF THE INVENTION

It is an object of the invention to provide an orthodontic device which permits the two treatment stages described hereinbefore to be combined in a single treatment and which permits an optimum result of the treatment to be achieved in a shorter time.

In an orthodontic device of the kind described first hereinbefore this object is accomplished in that that one of the upper and lower jaw thrust plates which carries the activating rods consists of two sections, which are interconnected by a jackscrew mechanism, and the activating rods are connected to the jackscrew mechanism. The other of the thrust plates is provided with slideways for cooperating with the activating rods and optionally also consists of two sections, which are interconnected by a jackscrew mechanism.

When it is desired to make the orthodontic device in accordance with the invention, a fixator is adjusted to a neutral bite position, i.e., the desired result of the correction of the sagittal supraocclusion is simulated in the fixator. The required sagittal displacement of the upper and lower jaws relative to each other can then be measured. A molding plate is slidably fitted on a jackscrew mechanism holder. In consideration of the measured extent of the required sagittal displacement, a pivotal movement is now imparted to the mounting plate on the gypsum model in accordance with the triangle of forces in such a manner that an angle corresponding to the required sagittal displacement is determined. That angle is used to define the inclined plane surface of the lower jaw thrust plate, which is then cast in the fixator and the activating rods carried by the jackscrew mechanism for the upper jaw thrust plate are then attached by means of wax to the inclined planar surface of the lower jaw thrust plate. As a result, the position of the jackscrew mechanism of the upper jaw thrust plate has been determined and the upper jaw thrust plate is subsequently cast in the fixator. The rods may have to be shortened in accordance with the anatomy of the patient. The device is subsequently inserted into the mouth in dependence on the simulated result of the treatment so that the opening and closing movement of the lower jaw relative to the upper jaw of the uncorrected jaws will cause one jaw to be subjected to a thrust as the rods run up on the inclined planar surface.

By means of such an arrangement the jackscrew mechanism can be used for a transversal correction by which the dental arch of one jaw is adjusted relative to the dental arch of the other jaw. At the same time a sagittal supraocclusion or subocclusion of the lower jaw relative to the upper jaw can be corrected by means of the activating rods, which are fixed to the jackscrew mechanism for the upper jaw and which are displaced in the transversal direction in case of a transversal expansion.

It is apparent that the treatment takes only one-half of the time previously required, and the result of the treatment is improved. Costs are saved also because only a single device is required.

BRIEF DESCRIPTION OF THE DRAWING

FIGS. 1 and 2 are, respectively, a side elevation and a top plan view showing a jackscrew mechanism provided with two guide rods.

FIGS. 3 and 4 are, respectively, a side elevation and a top plan view showing a jackscrew mechanism which is similar to that of FIGS. 1 and 2 but comprises activating rods which are welded to the jackscrew mechanism and extend at an angle to each other.

DETAILED DESCRIPTION OF THE PREFERRED EMBODIMENTS

Figure 5:
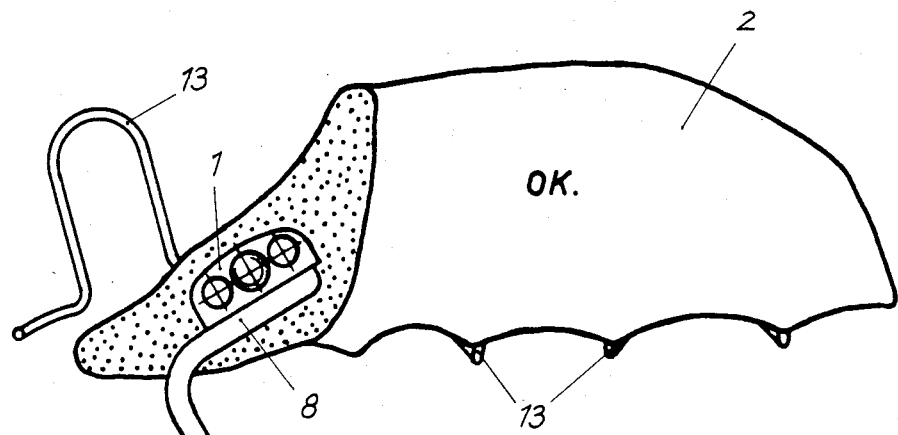
FIGS. 5 and 6 are side elevations coordinated with each other and show partly in section an opened orthodontic device comprising two thrust plates, each of which is provided with a jackscrew mechanism.

Preferred embodiments of the orthodontic device in accordance with the invention will now be described more in detail and reference to the drawing.

From FIGS. 1 to 4 it is apparent that the jackscrew mechanism 1 for the upper jaw thrust plate 2 consists in known manner of a jackscrew 3, which is screwed into two nut bodies 5, which are embedded in respective sections of the upper jaw thrust plate 2. Each of the nut bodies is formed on opposite sides of its female screw threads with two bores, which receive guide rods 4 for guiding the two nut bodies 5 relative to each other when the jackscrew mechanism 1 is being adjusted by a rotation imparted to the jackscrew 3 by means of its actuating head 6. Instead of two guides rods 4 and associated bores, a single guide rod and bore may be provided. Each nut body 5 is provided at its top with a flat 7, at which an angled member 8 consisting of flat wire is welded to the nut body 5. The protruding arm of each angled member 8 constitutes an activating rod 9. As is apparent from FIGS. 5 and 6, the activating rods 9 of the upper jaw thrust plate 2 cooperate with slide ways 10 of the lower jaw thrust plate 12. The latter may also consist of two sections, which are connected by a jackscrew mechanism 11. In accordance with FIGS. 3 and 4 those portions of the angled wire members 8a which are welded to the flats of the nut bodies 5 extend at an angle to each other and the activating rods 9a are parallel to each other. That design will be adopted if a relatively large transverse expansion is required.

It is apparent that the nut bodies 5 of the orthodontic device are formed with flats 7, to which the flat activating rods 8, 9 are secured, and each of the rods is angled and is secured at one arm to the jackscrew mechanism 1 in surface contact therewith. As a result, each thrust plate has a relatively small thickness so that it can be worn more conveniently by the patient. Besides, the lateral flats of the activating rods promote the fixation of the jackscrew mechanism 1 in the plastic plate body.

Figure 6:
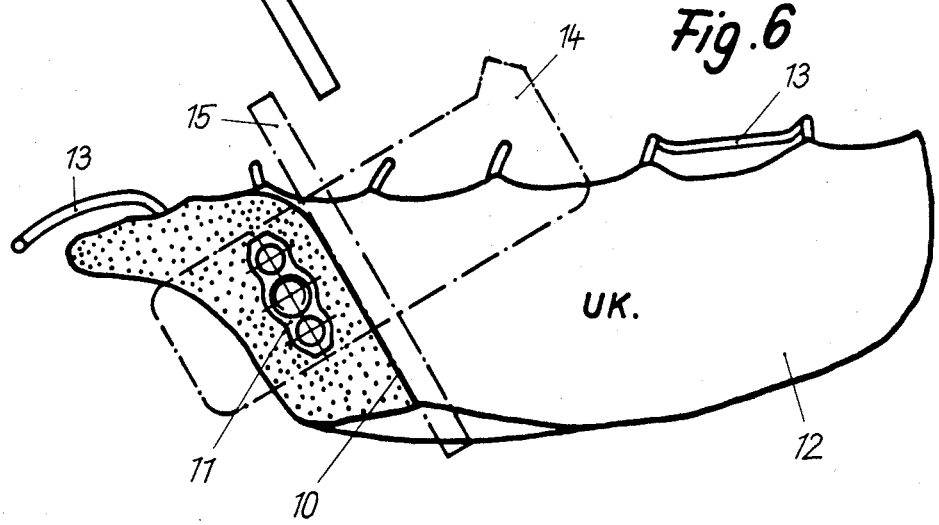

The arrangement of the jackscrew mechanism 1 and 11 in the upper jaw thrust plate 2 and the lower jaw thrust plate 12, respectively, is apparent from FIGS. 5 and 6. In this embodiment the activating rods 9 are provided in the upper plate and the slideways 10 on the lower one although that arrangement may be reversed, if desired. The upper jaw thrust plate 2 and the lower jaw thrust plate 12 will be secured to suitable teeth by means of wire loops.

Figure 10:
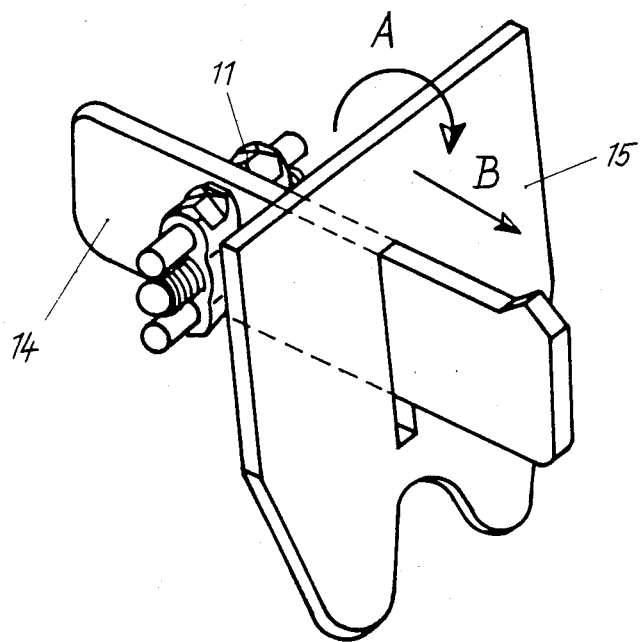
FIG. 10 is a perspective view showing a holder for a jackscrew mechanism in association with a molding plate.

FIG. 6 shows in phantom also the jackscrew mechanism holder 14, which is used to facilitate the casting of the lower jaw thrust plate 12 around its jackscrew mechanism 11. As in apparent from FIG. 10 holder 14 is provided with a molding plate 15, which is slidably fitted on the holder 14 to be pivotally movable in the direction indicated by the arrow A and displaceable in the direction indicated by the arrow B. That molding plate is used to form the slide ways 10 as the lower jaw thrust plate 12 is being cast.

Figure 7:
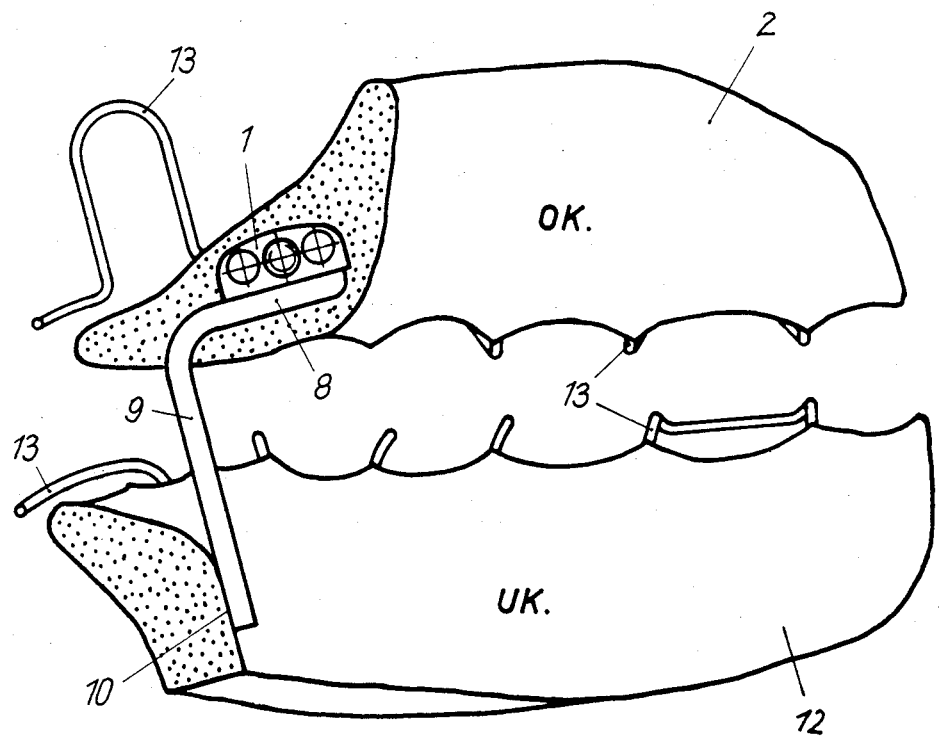
FIG. 7 is a side elevation showing a closed orthodontic device comprising two thrust plates and a jackscrew mechanism only in the lower jaw thrust plate.

FIG. 7 illustrates how the orthodontic device is activated in that the upper jaw thrust plate 2 provided with a jackscrew mechanism 1 and activating rods 9 cooperates with the lower jaw thrust plate 12, which is provided with slideways 10 but has no jackscrew mechanism in this case.

Figure 8:
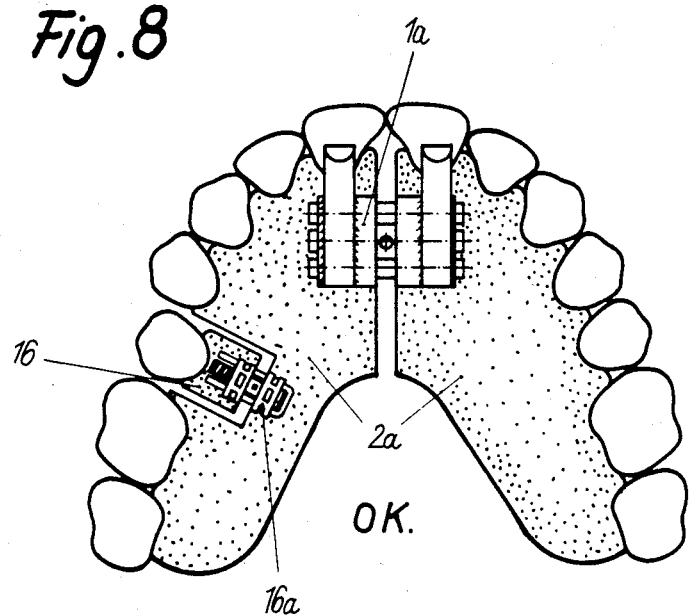
FIGS. 8 and 9 are coordinated top plan views showing the orthodontic device comprising upper and lower jaw thrust plates and additional means for correcting individual teeth.
Figure 9:
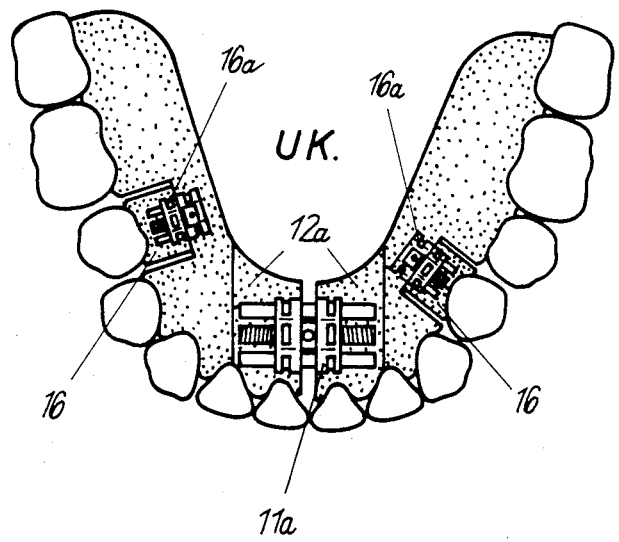

FIGS. 8 and 9 and are a top plan view showing an upper jaw thrust plate 2a and a lower jaw thrust plate 12a, each of which is provided with a jackscrew mechanism 1a or 11a. Means for correcting individual teeth are also shown and comprise correcting segments 16 and jackscrew mechanism 16a.

We claim:

1. In an orthodontic device for effecting a sagittal displacement of upper and lower jaws relative to each other, comprising
    an upper jaw thrust plate adapted to be secured to upper teeth,
    a lower jaw thrust plate to be secured to lower teeth,
    slideways provided on one of said thrust plates, and
    activating rods carried by the other of said thrust plates and inserted in said slideways in sliding contact therewith for effecting said sagittal displacement,
    the improvement residing in that
    said other thrust plate comprises two laterally spaced apart sections and
    a jackscrew mechanism which connects said two sections and is operable to transversely move said two sections relative to each other,
    said jackscrew mechanism comprising two nut bodies each of which is secured to one of said sections, each of said activating rods being carried by a respective one of said two nut bodies.

2. The improvement set forth in claim 1, wherein said one thrust plate also comprises two laterally spaced apart sections, which are interconnected by a further jackscrew mechanism, which is operable to transversely move said two sections of said one thrust plate relative to each other.

3. The improvement set forth in claim 1, wherein said jackscrew mechanism comprises actuating means, which are disposed and accessible between said two sections.

4. The improvement set forth in claim 1, wherein at least one of said thrust plates is provided with correcting segments for a correction of individual teeth.

5. The improvement set forth in claim 1, wherein each of said thrust plates is provided with wire loops for connecting said thrust plate to said teeth.

6. The improvement set forth in claim 1, further comprising, during casting of said one thrust plate, a holder of said jackscrew mechanism and a molding plate slidably mounted on said holder, which plate is displaceable and pivotally movable relative to said holder, so as to facilitate forming of said slideways on said one thrust plate.

7. A jackscrew mechanism for use in an orthodontic device for effecting a sagittal displacement of upper and lower jaws relative to each other, which orthodontic device comprises
    an upper jaw thrust plate adapted to be secured to upper teeth,
    a lower jaw thrust plate adapted to be secured to lower teeth,
    slideways provided on one of said thrust plates, and
    activating rods carried by the other of said thrust plates and adapted to cooperate with said slideways in sliding contact therewith for effecting said sagittal displacement, wherein
    said other thrust plate comprises two laterally spaced apart sections and
    said activating rods are carried by said jackscrew mechanism, which connects said two sections and is operable to transversely move said two sections relative to each other, said jackscrew mechanism comprising two nut bodies, each of which is adapted to be secured to one of said sections, and a jackscrew in screw-threaded engagement with both said nut bodies, each of said nut bodies being provided on one side with flats, and said activating rods comprising angled members consisting of flat wire and secured each to a respective one of said nut bodies, at said flats and having free end portions protruding from said nut portions for sliding contact with said slideways.

8. A jackscrew mechanism as set forth in claim 7, wherein said angled members have portions which extend at an angle to each other and are welded to said nut bodies at said flats and said free end portions are parallel to each other.

9. A process of manufacturing an orthodontic device for effecting a sagittal displacement of upper and lower jaws relative to each other, said device comprising an upper jaw thrust plate adapted to be secured to upper teeth, a lower jaw thrust plate adapted to be secured to lower teeth, slideways provided on one of said thrust plates, and activating rods carried by the other of said thrust plates and adapted to cooperate with said slideways in sliding contact therewith for effecting said sagittal displacement, each of said thrust plates comprises two laterally spaced apart sections, which are connected by a jackscrew mechanism, which is operable to transversely move said two sections relative to each other, and said activating rods are carried by said jackscrew mechanism of said other thrust plate, which process comprises providing a jackscrew mechanism holder, mounting one of said jackscrew mechanisms on said holder, slidably mounting on said holder a molding plate, which is displaceable and pivotally movable relative to said holder, casting said two sections of said one thrust plate around said one jackscrew mechanism on opposite sides of said holder when said molding plate is is a position to define a desired location and orientation of said slideways, inserting the activating rods of said other jackscrew mechanism in said slideways of said one thrust plate, and casting said two sections of said other thrust plate around the other of said jackscrew mechanism while said activating rods are held in said slideways.

* * * * *